United States Patent
Theucher (10) Patent No.: US 8,721,604 B2
(45) Date of Patent: May 13, 2014

(54) ASSEMBLY FOR A DRUG DELIVERY DEVICE AND DRUG DELIVERY DEVICE

(75) Inventor: Axel Theucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 192 days.

(21) Appl. No.: 13/311,423

(22) Filed: Dec. 5, 2011

(65) Prior Publication Data

US 2012/0150127 A1    Jun. 14, 2012

(30) Foreign Application Priority Data

Dec. 6, 2010 (EP) .................................... 10193752

(51) Int. Cl.
*A61M 5/00* (2006.01)

(52) U.S. Cl.
USPC .......................................... 604/246; 604/208

(58) Field of Classification Search
USPC .......................................... 604/207–210, 246
See application file for complete search history.

(56) References Cited

U.S. PATENT DOCUMENTS

| 6,193,698 | B1* | 2/2001 | Kirchhofer et al. | 604/211 |
| 2005/0137571 | A1* | 6/2005 | Hommann | 604/500 |
| 2006/0116647 | A1* | 6/2006 | Geiser et al. | 604/211 |
| 2008/0183139 | A1* | 7/2008 | Burren et al. | 604/211 |
| 2010/0331806 | A1* | 12/2010 | Plumptre et al. | 604/500 |
| 2012/0143146 | A1* | 6/2012 | Strehl et al. | 604/208 |
| 2012/0157966 | A1* | 6/2012 | Plumptre et al. | 604/506 |
| 2013/0131604 | A1* | 5/2013 | Avery | 604/207 |

FOREIGN PATENT DOCUMENTS

| DE | 3900926 | 8/1989 |
| EP | 0615762 | 9/1994 |
| EP | 1923083 | 5/2008 |
| WO | 96/07443 | 3/1996 |
| WO | 97/17096 | 5/1997 |
| WO | 99/03522 | 1/1999 |

OTHER PUBLICATIONS

European Search Report for EP Application No. 10193752, dated Apr. 28, 2011.

* cited by examiner

*Primary Examiner* — Nicholas Lucchesi
*Assistant Examiner* — Gerald Landry, II
(74) *Attorney, Agent, or Firm* — McDonnell Boehnen Hulbert & Berghoff LLP (57) ABSTRACT

An assembly for a drug delivery device is provided comprising a housing having a distal end and a proximal end, a dose button configured to be moved with respect to the housing for setting and delivering a dose of a drug from the device, and a blocking member. The blocking member is adapted and arranged to be releasably coupled to the housing such that, when the blocking member is coupled to the housing, movement of the dose button with respect to the housing is prevented. Furthermore, a drug delivery device is provided.

15 Claims, 7 Drawing Sheets

FIG 7B

ASSEMBLY FOR A DRUG DELIVERY DEVICE AND DRUG DELIVERY DEVICE

CROSS REFERENCE TO RELATED APPLICATIONS

The present application claims priority to European Patent Application No. 10193752.2 filed Dec. 6, 2010, the entire contents of which are incorporated herein by reference.

FIELD OF INVENTION

This disclosure relates to an assembly for a drug delivery device. The disclosure further relates to a drug delivery device comprising the assembly.

BACKGROUND

In a drug delivery device, often, a bung within a cartridge containing a plurality of doses of a drug is displaced by a piston rod. Thereby, a dose of the drug is expelled from the cartridge.

A drug delivery device is described in document EP 1 923 083 A1, for example.

It is an object of the present disclosure to provide an assembly facilitating provision of an improved drug delivery device, for example a device with increased safety for the user. Furthermore, an improved drug delivery device is provided.

This object may be achieved by the subject matter of the independent claims. Advantageous embodiments and refinements are subject matter of the dependent claims.

SUMMARY

One aspect relates to an assembly for a drug delivery device. The assembly may comprise a housing. The housing may have a distal end. The housing may have a proximal end. The assembly may comprise a dose button. The dose button may be configured to be moved with respect to the housing. In particular, the dose button may be moveable, preferably in an axial direction with respect to the housing, for setting and/or delivering a dose of a drug from the device. The assembly may comprise a blocking member. The blocking member may be adapted and arranged to be releasably coupled to the housing. In particular, the blocking member may be coupled to the housing such that, when the blocking member is coupled to the housing, movement of the dose button with respect to the housing may be prevented.

When coupled to the housing, the blocking member may be configured to prevent movement of the dose button in the proximal direction with respect to the housing for setting a dose of the drug. In this way, an unintentional dose setting operation may be prevented. User safety may be increased in this way.

According to an embodiment, when the blocking member and the housing are decoupled, a dose setting movement of the dose button with respect to the housing in the proximal direction from a distal end position into a dose delivery position is allowed.

When the blocking member and the housing are coupled, the dose button may be positioned in the distal end position. The blocking member may be operable to decouple, e.g. to disengage, from the housing. When the blocking member and the housing are decoupled, a dose setting operation may be allowed, in particular the dose button may be moveable from the distal end position in the proximal direction with respect to the housing.

According to an embodiment, the blocking member is moveable with respect to the housing for coupling and/or decoupling the blocking member and the housing. The blocking member may be moveable in the radial direction with respect to the housing. The blocking member may be moved in the radial inward direction with respect to the housing for decoupling the blocking member and the housing, thus enabling movement of the dose button in the proximal direction for setting the dose. The blocking member may be moved radially inwardly by a user for decoupling the blocking member and the housing.

According to an embodiment, the blocking member is a resilient member. Alternatively, the blocking member may be a resiliently mounted member. The resilient member or the resiliently mounted member may be configured such that a resilient force provided by the resilient member or the resiliently mounted member may move the blocking member in the radial outward direction with respect to the housing for coupling the blocking member to the housing when the dose button is moved in the distal direction for delivering the set dose.

During dose delivery, in particular at the end of the dose delivery operation, the blocking member may be automatically moveable in the radial outward direction. In particular, when the dose button was moved back into the distal end position during dose delivery, the blocking member may be automatically moved radially outwardly to couple with the housing due to the energy stored in the blocking member during the dose setting operation. When the dose button is out of the distal end position, radial outward movement of the blocking member may be prevented.

When the blocking member was moved radially outwardly, a subsequent dose setting operation may be prevented automatically until a further actuation of the blocking member takes place to decouple the blocking member and the housing. Unintentional dose setting may be prevented in this way. This may help to increase user safety.

According to an embodiment, the blocking member is decoupled from the housing when the dose button is out of the distal end position.

The blocking member may be operable to couple to the housing after dose delivery was completed, in particular when the dose button has reached the distal end position. The blocking member may be prevented from being moveable radially outwardly during the dose setting and/or the dose delivery operation, i.e. when the dose button is out of the distal end position. Unintentional coupling of the blocking member and the housing and, thus, interruption of a dose setting or dose delivery operation may be prevented in this way.

According to an embodiment, the blocking member is connected to or is integrated in the dose button.

The blocking member and the dose button may be formed unitarily. Manufacturing costs may be reduced in this way.

According to an embodiment, the blocking member is externally actuatable.

The blocking member may be accessible from the outside of the device. In particular, the blocking member may be actuatable by the user for moving the blocking member radially inwardly to decouple the blocking member and the housing. In this way, provision of a user-friendly device may be facilitated.

According to an embodiment, the assembly further comprises a resilient setting member, e.g. a spring. The assembly may be adapted and arranged to use an energy stored in the resilient setting member to drive the dose button proximally for setting a dose of the drug. In particular, the resilient setting member may be adapted and arranged to drive the dose button proximally when the blocking member is moved with respect to the housing for releasing the coupling of the blocking member and the housing.

The resilient setting member may provide an automatic dose setting operation when the blocking member and the housing were decoupled by the user. This may help to increase user comfort of the device.

According to an embodiment, the resilient setting member is arranged between a distal face of the dose button and a bearing member. The bearing member may be provided on an inner surface of the housing.

According to an embodiment, the housing comprises an engagement means. The engagement means may be adapted and arranged to mechanically cooperate with the blocking member when the dose button is in the distal end position. The engagement means may comprise an opening in the housing. The opening may be configured to receive the blocking member.

In particular, the blocking member may engage the opening when the dose button is in the distal end position. Due to mechanical cooperation, e.g. interlocking, of the blocking member and the opening, the dose button may be prevented from movement with respect to the housing.

According to an embodiment, the assembly comprises a drive member. The drive member may be moveable in the proximal direction with respect to the housing for setting a dose of the drug. The drive member may be moveable in the distal direction with respect to the housing for dispensing the set dose. Movement of the dose button may be converted into movement of the drive member with respect to the housing by mechanical cooperation of the dose button and the drive member.

The drive member may be permanently engaged with the dose button. The drive member may be adapted to operate through/within the housing. The drive member may be designed to translate axial movement through/within the drug delivery device.

According to an embodiment, the assembly comprises a piston rod. The piston rod may be adapted to operate through the housing. The piston rod may be adapted to transfer a force in the distal direction from the dose button. Movement of the dose button in the distal direction with respect to the housing may be converted into movement of the piston rod in the distal direction by means of mechanical interaction of the drive member and the piston rod for dispensing the dose.

The drive member may be releasably engaged with the piston rod. The piston rod may be adapted and arranged to translate axial, in particular distal, movement through/within the drug delivery device, preferably from the drive member to a bung of the device, for the purpose of dispensing a dose of the drug.

A further aspect relates to a drug delivery device. The drug delivery device may comprise the previously described assembly. The device may comprise a cartridge. The cartridge may hold a drug, preferably a plurality of doses of the drug.

The device may be a re-usable device. Alternatively, the device may be a disposable device. The previously described assembly may help to prevent an unintentional operation, e.g. a dose setting operation, of the device. In this way, provision of a user friendly drug delivery device may be facilitated.

According to a preferred embodiment, an assembly for a drug delivery device is provided, the assembly comprising a housing having a distal end and a proximal end, a dose button configured to be moved with respect to the housing for setting and delivering a dose of a drug from the device and a blocking member. The blocking member is adapted and arranged to be releasably coupled to the housing such that, when the blocking member is coupled to the housing, movement of the dose button with respect to the housing is prevented.

When coupled to the housing, the blocking member may be configured to prevent movement of the dose button in the proximal direction with respect to the housing for setting a dose of the drug. In this way, an unintentional dose setting operation may be prevented and, thus, user safety may be increased.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

Like elements, elements of the same kind and identically acting elements may be provided with the same reference numerals in the figures.

DETAILED DESCRIPTION

Figure 1:
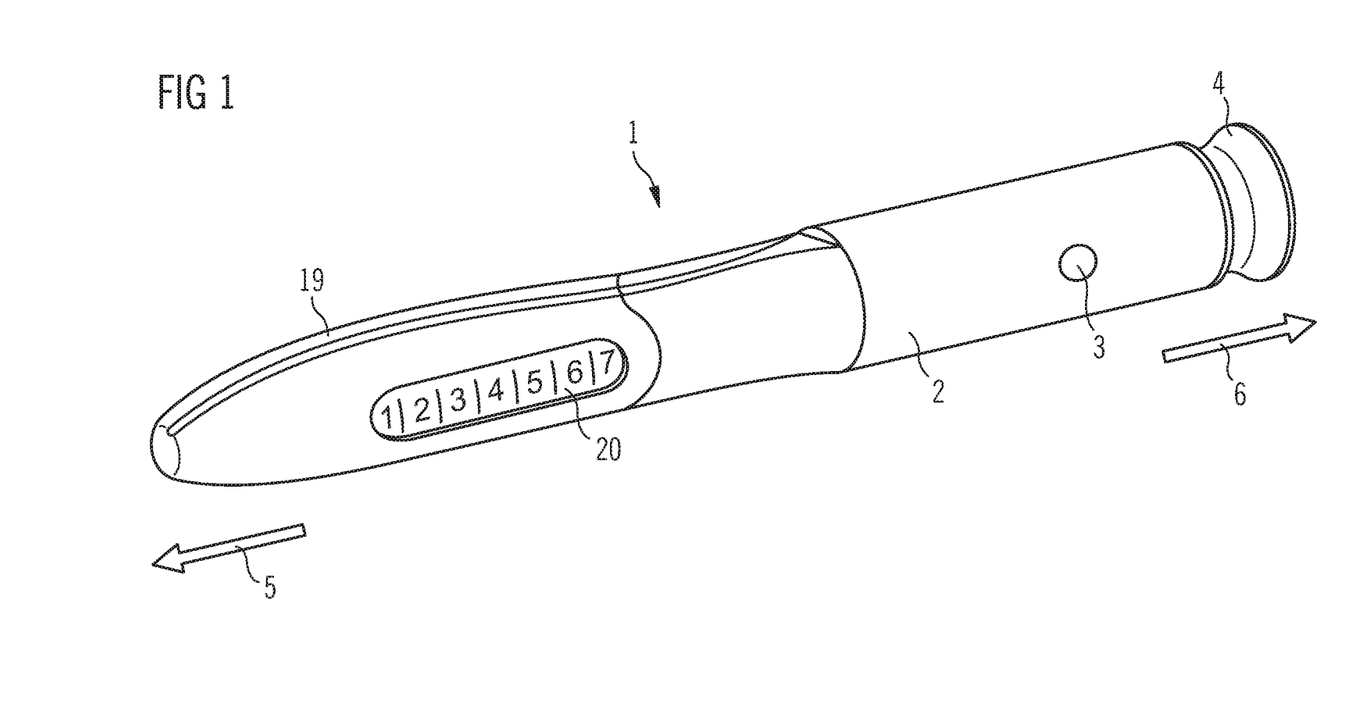
FIG. 1 schematically shows a perspective side view of a drug delivery device.
Figure 2:
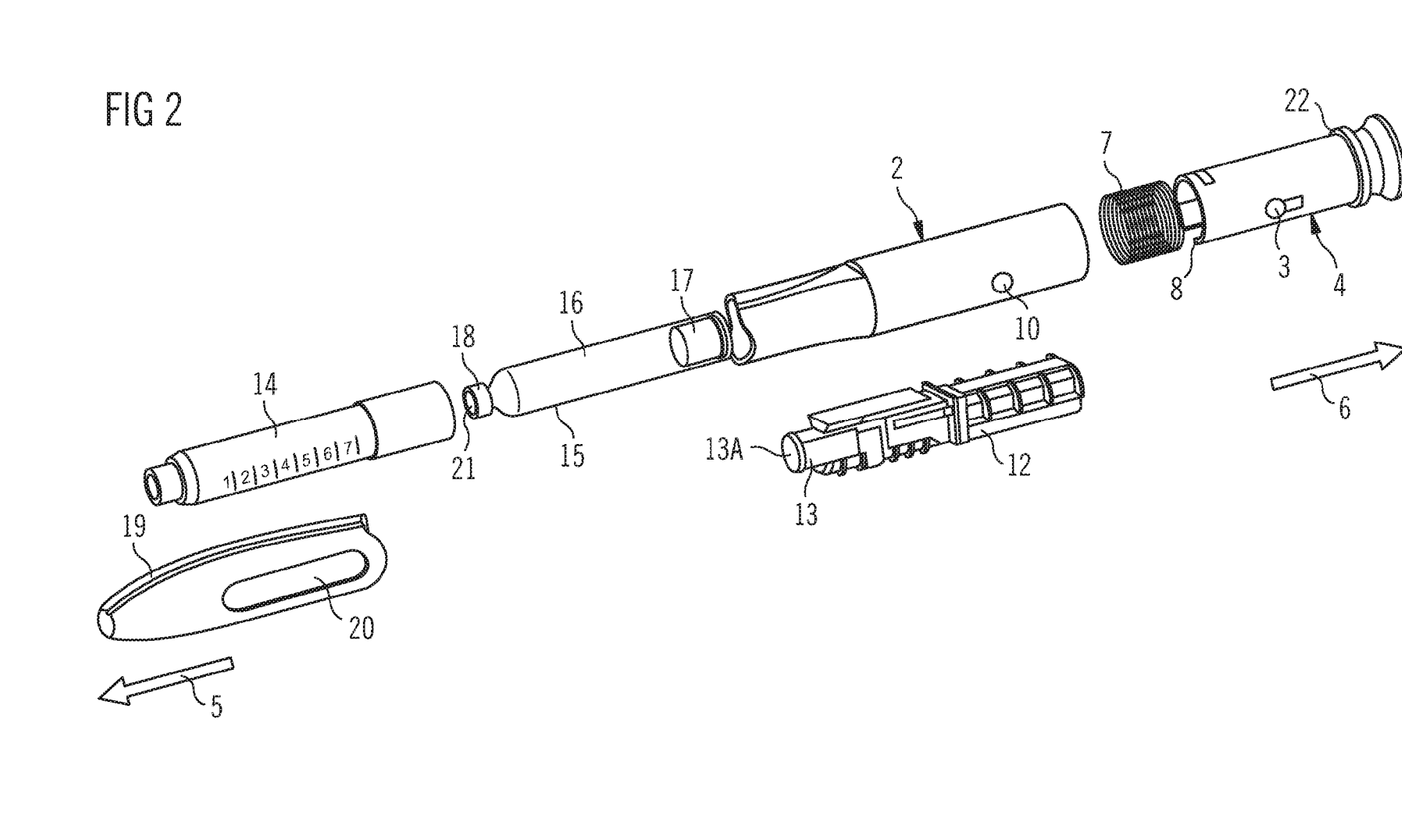
FIG. 2 schematically shows an exploded view of the drug delivery device of FIG. 1, FIG. 3 schematically shows a sectional side view of the drug delivery device of FIG. 1 before a dose setting operation takes place, FIG. 4 schematically shows a sectional side view of the drug delivery device of FIG. 1 before a dose delivery operation takes place, FIG. 5A schematically shows a perspective side view of a dose button, FIG. 5B schematically shows a sectional side view of the dose button of FIG. 5A, FIG. 6A schematically shows a perspective side view of a housing, FIG. 6B schematically shows a sectional side view of the housing of FIG. 6A, FIG. 7A schematically shows a perspective side view of a drive mechanism, FIG. 7B schematically shows a further perspective side view of the drive mechanism of FIG. 7A.

In FIGS. 1 and 2 a drug delivery device 1 is shown. The drug delivery device 1 comprises a housing 2. The drug delivery device 1 and the housing 2 have a distal end and a proximal end. The distal end is indicated by arrow 5. The proximal end is indicated by arrow 6. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the main longitudinal axis of the device 1.

The drug delivery device 1 comprises a cartridge 15. The cartridge 15 is permanently or releasably retained within a cartridge holder 14. The cartridge holder 14 stabilizes the cartridge 15 mechanically. The cartridge holder 14 may be, permanently or releasably, attached to the housing 2 of the drug delivery device 1. Alternatively, the cartridge 15 may be permanently or releasably fixed to the housing 2. In this case, the cartridge holder 14 may be redundant.

The cartridge 15 contains a drug 16, preferably a plurality of doses of the drug 16. The drug 16 may be a fluid drug. The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4 (1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, -continued

```
H-(Lys)6-des Pro36, Pro37, Pro38 [Trp(O2)25, Asp28] Exendin-4(1-39)-NH2,

H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;
``` or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 15 has an outlet 18. The outlet 18 is covered by a membrane 21. For delivery of the drug 16, the membrane 21 may be penetrated, for example pierced, e.g. by a needle assembly (not explicitly shown). A bung 17 is slideably retained within the cartridge 15. The bung 17 seals the cartridge 15 proximally. Movement of the bung 17 in the distal direction with respect to the cartridge 15 causes the drug 16 to be dispensed from the cartridge 15 through the outlet 18.

The device 1 comprises a dose button 4. The dose button 4 is moveable in the proximal direction, preferably from a distal end position into a dose delivery position, for setting a dose of the drug 16. The dose button 4 is moveable in the distal direction, preferably from the dose delivery position back into the distal end position, for dispensing the set dose. The dose button 4 may comprise or may be embodied as a sleeve.

Figure 5A:
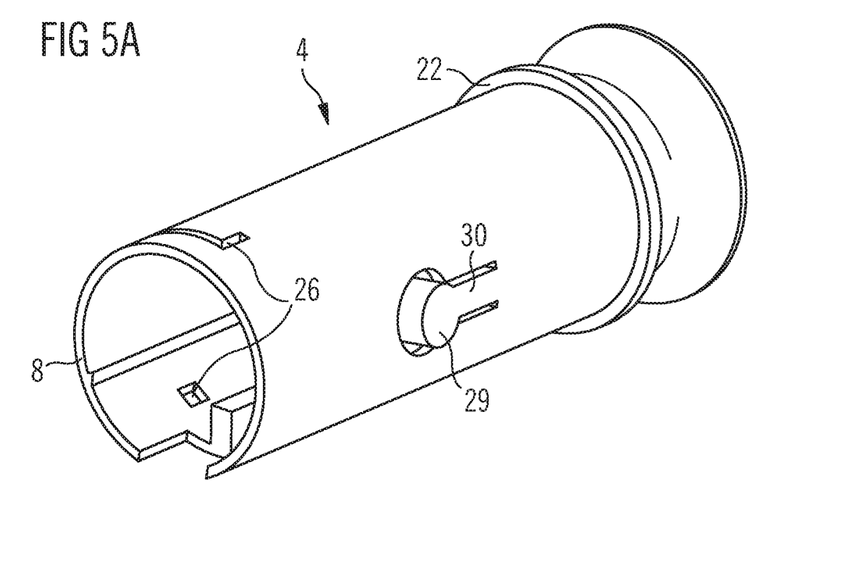
Figure 5B:
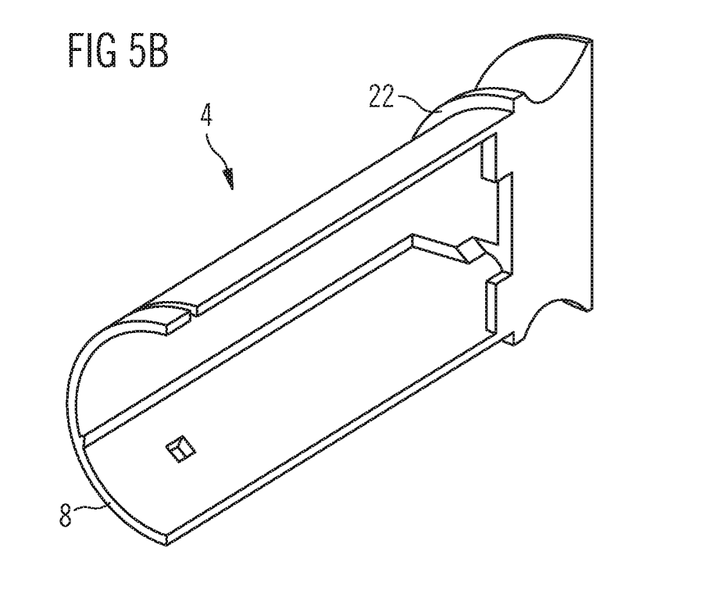
Figure 6A:
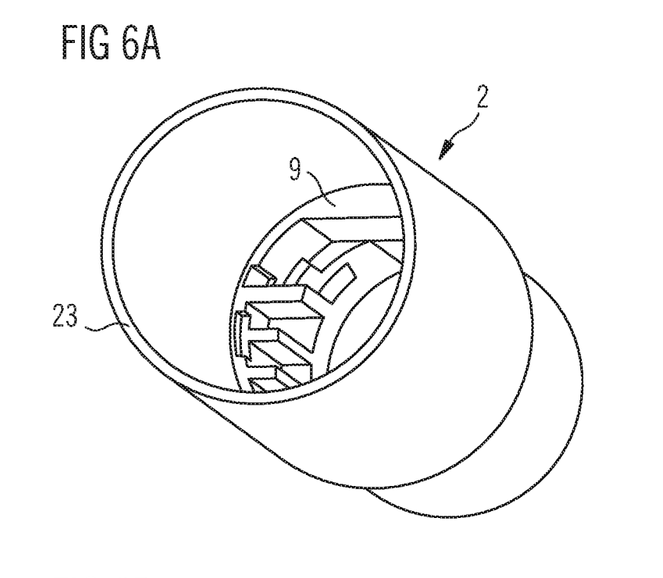
Figure 6B:
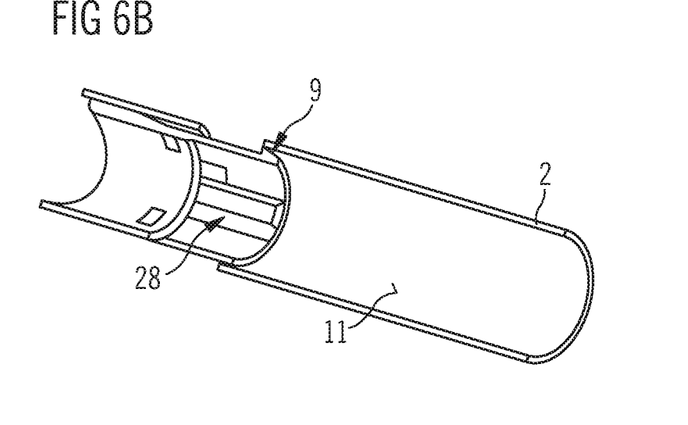

The dose button 4 comprises an interaction face 22 (see also FIGS. 5A and 5B). The interaction face 22 is arranged in the proximal section of the dose button 4. The interaction face 22 may be formed by a flange extending circumferentially around an outer surface of the dose button 4, for example. Mechanical cooperation of the interaction face 22 and a proximal face 23 of the housing 2 (see also FIGS. 6A and 6B) may prevent further movement of the dose button 4 in the distal direction when the dose button 4 is in the distal end position. Accordingly, the interaction face 22 of the dose button 4 may provide a distal end stop for the dose button 4.

Figure 7A:
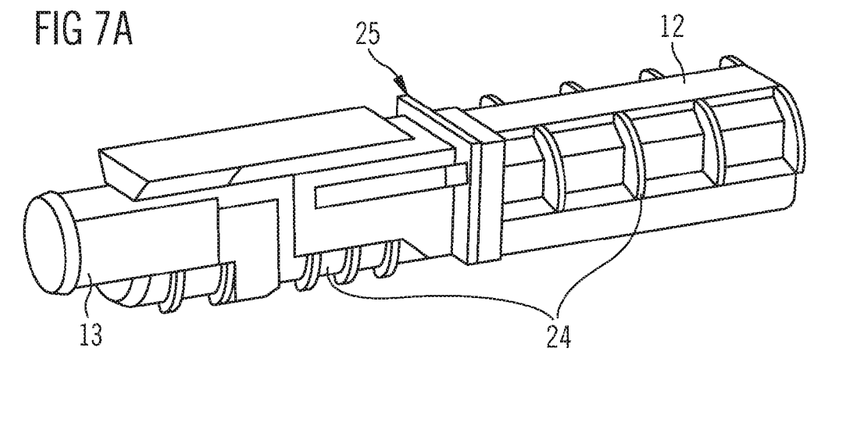
Figure 7B:
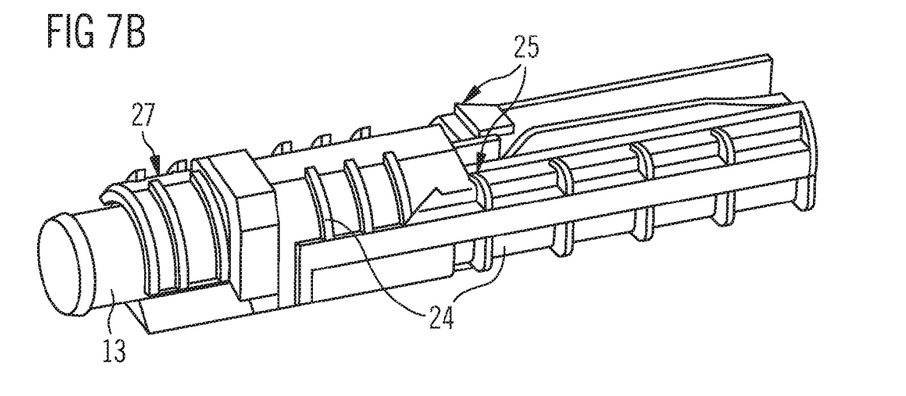

The device comprises a drive mechanism 24 (see FIGS. 7A and 7B). The drive mechanism 24 comprises a drive member 12. The drive member 12 and the dose button 4 are secured to each other to prevent rotational and/or axial movement between one another. The drive member 12 comprises engaging means 25 (see FIGS. 7A and 7B). Engaging means 25 may comprise a rib, preferably a plurality of ribs. The dose button 4 comprises mating engaging means 26 (see FIGS. 5A and 5B). Engaging means 25 may comprise a nut, preferably a plurality of nuts. Movement of the dose button 4 is converted into movement of the drive member 12 with respect to the housing 2 by mechanical cooperation of the engaging means 25 and the mating engaging means 26. The drive member 12 transfers movement of the dose button 4 into movement of a piston rod 13 for dispensing the dose by mechanical cooperation of the drive member 12 and the piston rod 13. The drive member 12 extends about the piston rod 13 (see FIGS. 7A and 7B).

The piston rod 13 is designed to operate through the housing 2 of the drug delivery device 1. The piston rod 13 is designed to transfer axial movement through the drug delivery device 1 for the purpose of delivering the drug 16. The piston rod 13 is configured to be axially displaced in the distal direction for delivering the dose. Preferably, the piston rod 13 is prevented from being axially displaced in the proximal direction when setting a dose of the drug 4 by mechanical cooperation with a fixed part of the drive mechanism 24. A bearing surface 13A located at the distal end of the piston rod 13 is disposed to abut the proximal face of the bung 17.

The fixed part of the drive mechanism 24 comprises a locking member 27 (see FIG. 7B). A mating locking member 28 (see FIG. 6B) may be provided on the inner surface 11 of the housing 2. Movement of the fixed part with respect to the housing 2 may be prevented by mechanical cooperation of locking member 27 and mating locking member 28. The fixed part mechanically cooperates with the drive member 12, e.g. by providing teeth for mechanical interaction with a gear wheel of the drive member 12. More details concerning the drive mechanism 24 can be taken from document WO 08058666 A1 the disclosure of which is incorporated herein by reference.

The device 1 comprises a cap 19. The cap 19 is configured to cover the distal end of the device 1. The cap 19 comprises a window aperture 20. A dosing scale provided on the cartridge holder 14 and/or the cartridge 15 may be visible through the window aperture.

The device 1 comprises a resilient setting member 7. The resilient setting member 7 may be spring, e.g. a compression spring. The resilient setting member 7 exerts a force, in particular a proximally directed force, onto the dose button 4. An energy stored in the resilient setting member 7, either during assembly or during a dose delivery operation, may be used for driving the dose button 4 proximally for setting a dose of the drug 16, which is explained later on in more detail. The resilient setting member 7 is provided between a distal face 8 of the dose button 4 and a bearing member 9. The bearing member 9 is provided on an inner surface 11 of the housing 2 (see, in particular FIGS. 5A, 5B and FIGS. 6A, 6B). The bearing member 8 may be a protrusion or a nut provided circumferentially on the inner surface 11 of the housing 2.

The device 1 comprises a blocking member 3. The blocking member 3 is configured to mechanically interact with the housing 2. The blocking member 3 is adapted and arranged to be releasably coupled to the housing 2. The housing 2 comprises an engagement means 10, e.g. an opening. Said engagement means 10 is configured to receive the blocking member 3 for coupling the blocking member 3 and the housing 2. Thus, an interlock of engagement means 10 and blocking member 3 is formed. The blocking member 3 and the housing 2 are coupled to one another when the dose button 4 is in the distal end position (see FIG. 3).

When the blocking member 3 is coupled to the housing 2, movement of the dose button 4 with respect to the housing 2, in particular movement driven by the energy stored in the resilient setting member 7, is prevented. When the blocking member 3 and the housing 2 are decoupled, a dose setting movement of the dose button 4 with respect to the housing 2 in the proximal direction is allowed. Furthermore, when the blocking member 3 and the housing 2 are decoupled, a dose delivery movement of the dose button 4 with respect to the housing 2 in the distal direction, in particular towards a distal end position is allowed. Operation of setting and delivering a dose and, in particular, operation of the blocking member 3 is described in detail in connection with FIGS. 3 and 4.

The blocking member 3 is prevented from axial and rotational movement with respect to the dose button 4. The blocking member 3 is connected to or is integrated in the dose button 4. The blocking member 3 is externally actuatable, in particular user actuatable. The blocking member 3 is moveable with respect to the housing 2 for coupling and/or decoupling the blocking member 3 and the housing 2. In particular, the blocking member 3 is moveable in the radial direction with respect to the housing 2. The blocking member 3 is moveable in the radial inward direction with respect to the housing 2, preferably by the user, for decoupling the blocking member 3 and the housing 2.

The blocking member 3 is moveable in the radial outward direction with respect to the housing 2 for coupling the blocking member 3 and the housing 2, thus preventing movement of the dose button 4 with respect to the housing 2.

The blocking member 3 comprises a resilient member or a resiliently mounted member. A resilient force provided by the resilient member or the resiliently mounted member automatically moves the blocking member 3 in the radial outward direction with respect to the housing 2 for coupling the blocking member 3 to the housing 2 when the dose button 4 is in the distal end position, which is explained later on in more detail. The blocking member 3 comprises a knob 29. The knob 29 is connected to the dose button 4 by means of a flexible web 30 (see FIG. 5A). When the dose button 4 is in the distal end position, the knob 29 protrudes from the outer surface of the housing 2. Accordingly, the blocking member 3 is accessible from the outside of the device 1 when the dose button 4 is in the distal end position.

Figure 3:
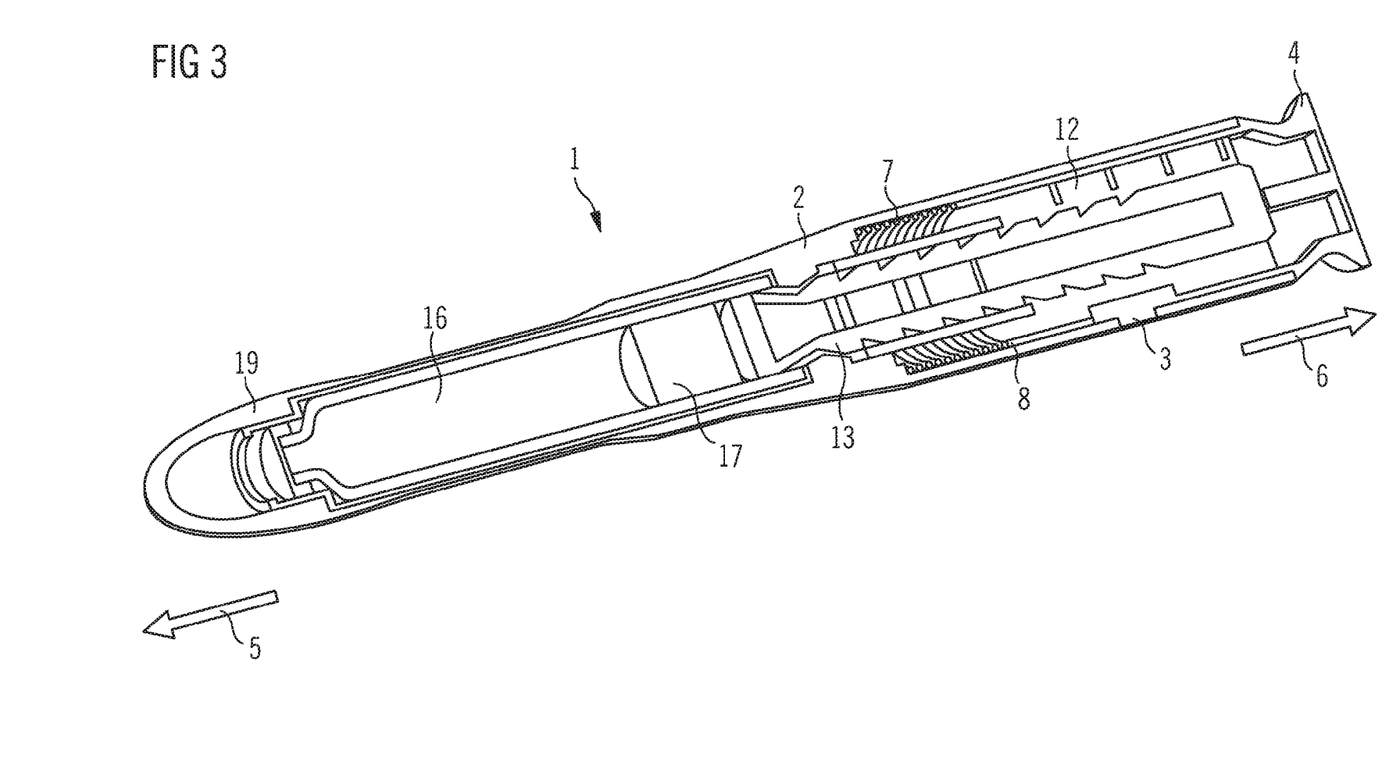

FIG. 3 schematically shows a sectional side view of the drug delivery device of FIG. 1 before a dose setting operation takes place.

Figure 4:
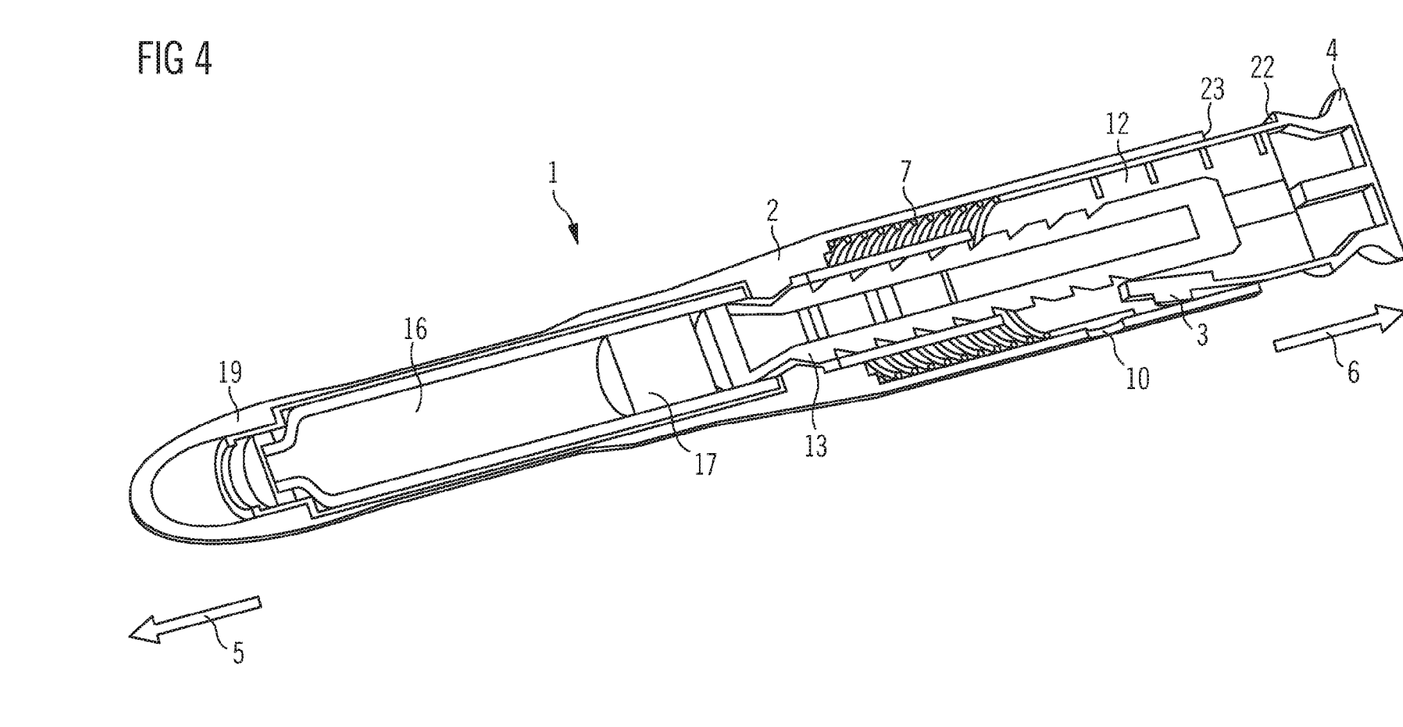

FIG. 4 schematically shows a sectional side view of the drug delivery device of FIG. 1 before a dose delivery operation takes place.

In an initial state of the device 1, e.g. the state of the device 1 when the device 1 is supplied to the user as assembled by the manufacturer, the dose button 4 is positioned in the distal end position as shown in FIG. 3. The housing 2 and the blocking member 3 are coupled to one another due to mechanical cooperation of the blocking member 3 and the engagement means 10 and, thus, movement of the dose button 4 with respect to the housing 2 is prevented. The resilient setting member 7 is biased, e.g. compressed.

For setting a dose, the user presses knob 29 and, thus, moves the blocking member 3 radially inwardly with respect to the housing 2. Thereby, the blocking member 3 decouples from the housing 2, in particular from the engagement means 10. When the blocking member 3 is moved radially inwardly, an energy is stored in the blocking member 3. When the blocking member 3 was moved radially inwardly, the blocking member 3 provides a resilient force. The force is directed radially outwardly with respect to the housing 2.

When the blocking member 3 and the housing 2 are decoupled, the dose button 4 is moveable with respect to the housing 2. Accordingly, the resilient setting member 7 is allowed to relax, thereby moving the dose button 4 proximally out of the distal end position and into the dose delivery position (see FIG. 4). A proximal end stop (not explicitly shown) may be provided in the housing, e.g. in a proximal section of the housing 2, to prevent movement of the dose button 4 in the proximal direction beyond the dose delivery position by mechanical cooperation of the proximal end stop and the dose button 4.

When the dose button 4 is out of the distal end position, the blocking member 3 is prevented from moving radially outwardly driven by the energy stored in the blocking member 3 due to mechanical cooperation of the blocking member 3 and the inner surface 11 of the housing 2. When the dose button 4 is out of the distal end position, the blocking member 3 may be guided along a guide track arranged on the inner surface 11 of the housing 2 (not explicitly shown).

For delivering the set dose, the user pushes onto the dose button 4, thereby moving the dose button 4 distally. Thereby, the resilient setting member 7 is compressed. The dose button 4 is moved distally until the interaction face 22 of the dose button 4 abuts the proximal face 23 of the housing 2. When the interaction face 22 of the dose button 4 abuts the proximal face 23 of the housing 2, the dose button 4 is in the distal end position and the set dose of the drug 16 was dispensed completely from the device 1.

When the dose button 4 is in the distal end position, the blocking member 3 and the engagement means 10 axially overlap. Accordingly, due to the energy stored in the blocking member 3, the blocking member 3 is automatically moved radially outwardly such that the blocking member 3 mechanically cooperates with the engagement means 10 and such that the dose button 4 is prevented from proximal movement with respect to the housing 2 until the user actuates again the blocking member 3 for setting a subsequent dose of the drug 16.

The drug delivery device 1 may be a pen-type device, in particular a pen-type injector. The device 1 may be a disposable or a re-usable device. The device 1 may be especially suitable for dispensing fixed doses of the drug 16, e.g. doses the size of which may not be varied by the user. Accordingly, the dose button 4 may be moved by the same distance in the proximal direction with respect to the housing 2 during each dose setting operation.

The invention claimed is:

1. An assembly for a drug delivery device, comprising
a housing having a distal end and a proximal end,
a dose button configured to be moved with respect to the housing for setting and delivering a dose of a drug from the device,
a blocking member,
wherein the blocking member is adapted and arranged to be releasably coupled to the housing such that, when the blocking member is coupled to the housing, movement of the dose button with respect to the housing is directly prevented.

2. The assembly according to claim 1, wherein, when the blocking member and the housing are decoupled, a dose setting movement of the dose button with respect to the housing in the proximal direction from a distal end position into a dose delivery position is allowed.

3. The assembly according to claim 2, wherein the blocking member is decoupled from the housing when the dose button is out of the distal end position.

4. The assembly according to claim 1, wherein the blocking member is moveable with respect to the housing for coupling and/or decoupling the blocking member and the housing.

5. The assembly according to claim 4, wherein the blocking member is moveable in the radial direction with respect to the housing, and wherein the blocking member is moved in the radial inward direction with respect to the housing for decoupling the blocking member and the housing.

6. The assembly according to claim 5, wherein the blocking member is a resilient member or a resiliently mounted member configured such that a resilient force provided by the resilient member or the resiliently mounted member moves the blocking member in the radial outward direction with respect to the housing for coupling the blocking member to the housing when the dose button is moved in the distal direction for delivering the set dose.

7. The assembly according to claim 1, wherein the blocking member is connected to or is integrated in the dose button.

8. The assembly according to claim 1, wherein the blocking member is externally actuatable.

9. The assembly according to claim 1, further comprising a resilient setting member, wherein the assembly is adapted and arranged to use an energy stored in the resilient setting member to drive the dose button proximally for setting a dose of the drug.

10. The assembly according to claim 9, wherein the resilient setting member is arranged between a distal face of the dose button and a bearing member provided on an inner surface of the housing.

11. The assembly according to claim 2, wherein the housing comprises an engagement means which is adapted and arranged to mechanically cooperate with the blocking member when the dose button is in the distal end position.

12. The assembly according to claim 11, wherein the engagement means comprises an opening in the housing which is configured to receive the blocking member.

13. The assembly according to claim 1, comprising a drive member which is moveable in the proximal direction with respect to the housing for setting a dose of the drug and moveable in the distal direction with respect to the housing for dispensing the set dose, wherein movement of the dose button is converted into movement of the drive member with respect to the housing by mechanical cooperation of the dose button and the drive member.

14. The assembly according to claim 13, comprising a piston rod adapted to operate through the housing and to transfer a force in the distal direction from the dose button, wherein movement of the dose button in the distal direction with respect to the housing is converted into movement of the piston rod in the distal direction by means of mechanical interaction of the drive member and the piston rod for dispensing the dose.

15. A drug delivery device comprising the assembly according to claim 1, wherein the device comprises a cartridge holding a drug.

* * * * *

UNITED STATES PATENT AND TRADEMARK OFFICE
CERTIFICATE OF CORRECTION

PATENT NO.       : 8,721,604 B2
APPLICATION NO.  : 13/311423
DATED            : May 13, 2014
INVENTOR(S)      : Axel Teucher Page 1 of 1

It is certified that error appears in the above-identified patent and that said Letters Patent is hereby corrected as shown below:

On the title page, at (12): please delete "Theucher" and insert -- Teucher --.

On the title page, under (75) Inventor: please delete "Theucher" and insert -- Teucher -- after "Axel".

Signed and Sealed this
Nineteenth Day of April, 2016

Michelle K. Lee
*Director of the United States Patent and Trademark Office*